(12) United States Patent
Harte et al.

(10) Patent No.: US 12,690,927 B2
(45) Date of Patent: Jul. 28, 2026

(54) MARKERLESS NAVIGATION USING AI COMPUTER VISION

(71) Applicant: Healthcare Outcomes Performance Company Limited, Altrincham (GB)

(72) Inventors: Thomas Harte, London (GB); Huy Quoc Phan, Fleet (GB)

(73) Assignee: Healthcare Outcomes Performance Company Limited, Altrincham (GB)

( * ) Notice: Subject to any disclaimer, the term of this patent is extended or adjusted under 35 U.S.C. 154(b) by 0 days.

(21) Appl. No.: 19/061,870

(22) Filed: Feb. 24, 2025

(65) Prior Publication Data

US 2025/0186137 A1     Jun. 12, 2025

Related U.S. Application Data

(63) Continuation of application No. 18/509,079, filed on Nov. 14, 2023, now Pat. No. 12,251,173, which is a
(Continued)

(51) Int. Cl.
G06T 7/73     (2017.01)
A61B 34/20     (2016.01)
(Continued)

(52) U.S. Cl.
CPC .............. *A61B 34/20* (2016.02); *A61B 90/39* (2016.02); *G06N 3/08* (2013.01); *G06T 7/10* (2017.01); *G06T 7/74* (2017.01); *A61B 2034/2057* (2016.02); *A61B 2034/2065* (2016.02); *A61B 2090/3945* (2016.02);
(Continued)

(58) Field of Classification Search
None
See application file for complete search history.

(56) References Cited

U.S. PATENT DOCUMENTS

| | | | |
|---|---|---|---|
| 10,724,853 B2 | 7/2020 | Bernstein et al. | |
| 10,890,439 B2 | 1/2021 | Bernstein et al. | |
| | (Continued) | | |

FOREIGN PATENT DOCUMENTS

| | | | |
|---|---|---|---|
| WO | WO-2020163355 A1 * | 8/2020 | ............... G06N 5/01 |
| WO | WO-2021220060 A2 | 11/2021 | |

OTHER PUBLICATIONS

GB2217901.4 Examination Report under Section 18(3) dated Jun. 28, 2023.
(Continued)

*Primary Examiner* — Idowu O Osifade
(74) *Attorney, Agent, or Firm* — Wilson Sonsini Goodrich & Rosati

(57)     ABSTRACT

Provided herein are devices, systems, and methods for a three-dimensional registering, tracking, and/or guiding an object of interest, such a body part, a surgical tool, or an implant, during a surgical procedure. Such devices, systems, and methods may offer minimally invasive, high precision registering, tracking, and/or guiding of the object of interest using a patterned light beam and data processing using artificial intelligence. The methods, devices, and systems disclosed herein may be compatible with a simple marker or markers placed by a minimally invasive method on the object of interest.

20 Claims, 16 Drawing Sheets

Related U.S. Application Data continuation of application No. 17/243,333, filed on Apr. 28, 2021, now Pat. No. 11,857,271.

(60) Provisional application No. 63/017,447, filed on Apr. 29, 2020, provisional application No. 63/074,338, filed on Sep. 3, 2020.

(51) Int. Cl.
| | |
|---|---|
| *A61B 90/00* | (2016.01) |
| *G06N 3/08* | (2023.01) |
| *G06T 7/10* | (2017.01) |

(52) U.S. Cl.
CPC ................. *A61B 2090/3983* (2016.02); *G06T 2207/20081* (2013.01); *G06T 2207/20084* (2013.01)

(56) References Cited

U.S. PATENT DOCUMENTS

| | | | |
|---|---|---|---|
| 11,551,032 B1 | 1/2023 | Gebhardt et al. | |
| 11,852,461 B2 | 12/2023 | Bernstein et al. | |
| 11,857,271 B2 | 1/2024 | Harte et al. | |
| 12,169,123 B2 | 12/2024 | Bernstein et al. | |
| 2013/0060146 A1 | 3/2013 | Yang et al. | |
| 2018/0049622 A1 | 2/2018 | Ryan et al. | |
| 2019/0000564 A1 | 1/2019 | Navab et al. | |
| 2019/0380792 A1* | 12/2019 | Poltaretskyi | G06N 3/08 |
| 2021/0338339 A1 | 11/2021 | Harte et al. | |
| 2022/0346875 A1* | 11/2022 | Khan | A61B 18/20 |
| 2023/0237740 A1 | 7/2023 | Haslam et al. | |
| 2024/0046490 A1* | 2/2024 | Lang | A61B 90/361 |
| 2024/0081917 A1 | 3/2024 | Harte et al. | |
| 2024/0102795 A1 | 3/2024 | Bernstein et al. | |
| 2025/0116511 A1 | 4/2025 | Bernstein et al. | |

OTHER PUBLICATIONS

GB2217901.4 Search Report under Section 17(6) dated Sep. 29, 2023.

GB2401710.5 Combined Search and Examination Report under Section 17 & 18(3) dated May 21, 2024.

Gerig, Guido. Structured-Lighting. CS 6320, 3D Computer Vision Spring 2012. Slide Serve. 51 pages/slides (2012). Available at https://www.slideserve.com/august/structured-lighting.

Movimed. What is Laser Triangulation? 3 pages. Dec. 23, 2018. Available at https://web.archive.org/web/20181223092133/https://www.movimed.com/knowledgebase/what-is-laser-triangulation/.

Navio. Smith&Nephew. https://www.smith-nephew.com/professional/microsites/navio/, 2 pages total (Accessed on Dec. 30, 2020).

NDI. Optical Measurement Products. https://www.ndigital.com/products/ , 7 pages total (Accessed on Dec. 29, 2020).

PCT/IB2021/000329 International Preliminary Report on Patentability dated Oct. 27, 2022.

PCT/IB2021/000329 International Search Report and Written Opinion dated Nov. 17, 2021.

PCT/IB2021/000329 Invitation to pay additional Fees dated Sep. 27, 2021.

Stemmer Imaging. Smart Vision Lights Structured Light Pattern Projectors. 4 pages (Aug. 12, 2020). Available at https://web.archive.org/web/20200812034915/https://www.stemmer-imaging.com/en-gb/products/series/smart-vision-lights-structured-light/.

Stemmer Imaging. Z-Laser ZX: High accuracy laser modules. 3 pages (Aug. 8, 2020). Available at https://web.archive.org/web/20200808181418/https://www.stemmer-imaging.com/en-gb/products/series/z-laser-zx/.

Stryker. Mako—Robotic-Arm Assisted Surgery. https://www.stryker.com/us/en/portfolios/orthopaedics/joint-replacement/mako-robotic-arm-assisted-surgery.html, 3 pages total, Last Updated Sep. 2020 (Accessed on Dec. 30, 2020).

U.S. Appl. No. 17/243,333 Notice of Allowance dated Aug. 15, 2023.

U.S. Appl. No. 18/509,079 Notice of Allowance dated Nov. 21, 2024.

Vicon. Award Winning Motion Capture Systems. 8 pages total (Nov. 1, 2020). Available at https://web.archive.org/web/20201101063929/https://www.vicon.com/.

* cited by examiner (A) Algorithm 1

(B) Algorithm 2

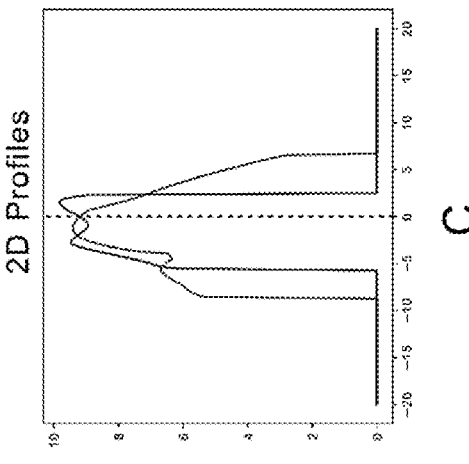
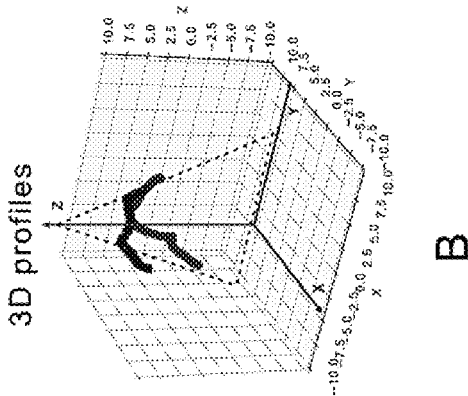
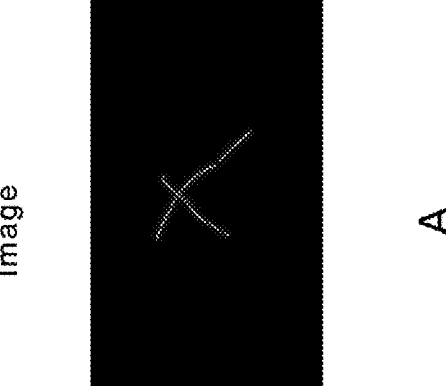
FIG. 10

After Fitting

Before Fitting

ICP fitting

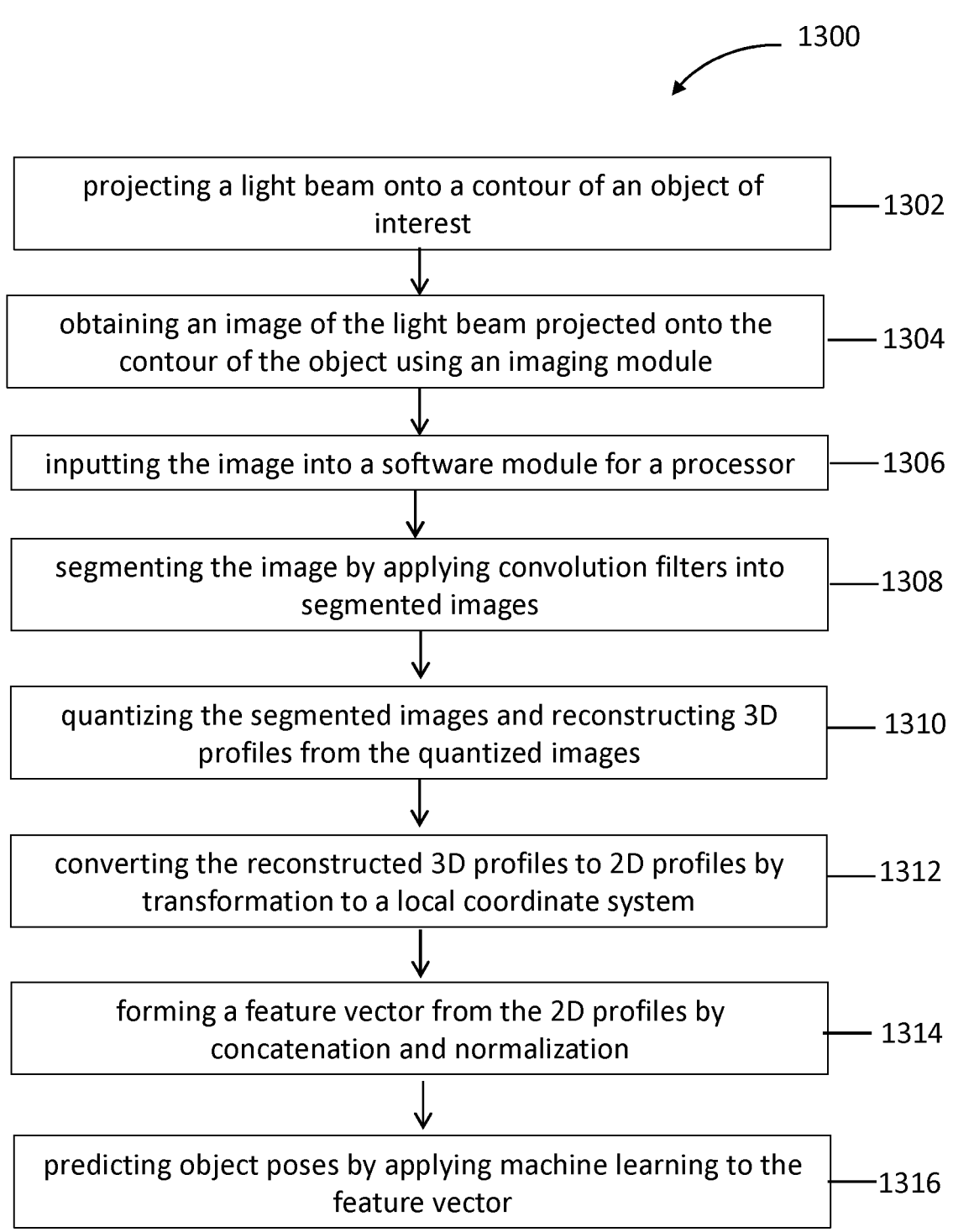

1300 projecting a light beam onto a contour of an object of interest —1302 obtaining an image of the light beam projected onto the contour of the object using an imaging module —1304 inputting the image into a software module for a processor —1306 segmenting the image by applying convolution filters into segmented images —1308 quantizing the segmented images and reconstructing 3D profiles from the quantized images —1310 converting the reconstructed 3D profiles to 2D profiles by transformation to a local coordinate system —1312 forming a feature vector from the 2D profiles by concatenation and normalization —1314 predicting object poses by applying machine learning to the feature vector —1316

FIG. 13

MARKERLESS NAVIGATION USING AI COMPUTER VISION

CROSS-REFERENCE

This application is a continuation of U.S. patent application Ser. No. 18/509,079, filed Nov. 14, 2023, which is a continuation of U.S. patent application Ser. No. 17/243,333, filed Apr. 28, 2021, now U.S. Pat. No. 11,857,271, issued Jan. 2, 2024, which claims the benefit of priority from U.S. Provisional Application No. 63/017,447, filed Apr. 29, 2020, and U.S. Provisional Application No. 63/074,338, filed Sep. 3, 2020, all of which are incorporated herein by reference in their entirety.

BACKGROUND

The ability to provide three-dimensional registering, tracking, and/or guiding an object of interest, such as a body part, a surgical tool, or an implant, during a surgical procedure may offer a powerful tool in improving surgical outcomes. An accurate, real-time, three-dimensional surgical navigation may allow a system for robotic surgery or robotic-assisted surgery to better understand its environment and perform more accurately. Usually, robot-assisted surgical systems rely on a marker-based tracking and a triangulation approach to track tools and body parts, which may often lead to prolonged surgical time and a less favorable outcome for the patient. Devices, systems, and methods having the capability for minimally invasive, high precision registering, tracking, and/or guiding of the object of interest would be valuable in improving surgical outcomes.

SUMMARY

Described herein are devices, methods, and systems addressing a need for minimally invasive, high precision registering, tracking, and/or guiding of an object of interest during a surgical procedure to improve the performance and the outcomes of the surgery for a patient.

Provided herein are methods for tracking an object of interest comprising: (a) aiming a light beam from a light source at the object of interest, (b) projecting the light beam onto a contour of the object of interest; (c) obtaining an image of the light beam projected onto the contour of the object of interest using an imaging module; (d) inputting data of the image into a software module for a processor; and (e) analyzing the data of the image to determine at least one of location, orientation, and rotation of the object of interest in three-dimensional space using the software module. In some embodiments, the object of interest comprises a body part of a subject. In some embodiments, the body part comprises bones of a joint. In some embodiments, the method occurs during a surgical procedure.

In some embodiments, the light beam from the light source passes through a patterned filter. In some embodiments, the patterned filter has a patterned slit in a crosshair shape and the light beam has a crosshair pattern. In some embodiments, the light beam from the source comprises one or more wavelengths.

In some embodiments, the analyzing step comprises segmenting the data of the image into at least two segmented data of the image by convolution. In some embodiments, the analyzing step comprises applying a first set of a predetermined number (N) of convolution filters to the data of the image to generate a predetermined number (N) of first filtered images. In some embodiments, the convolution filter comprises a two-dimensional convolution filter of $D \times D \times 1$ dimension. In some embodiments, the first filtered images are merged into a first merged image by applying a $D \times D \times N$ filter. In some embodiments, a second set of the predetermined number (N) of convolution filters is applied to the first merged image to generate the predetermined number of second filtered images. In some embodiments, the second filtered images are merged into a second merged image by applying a $D \times D \times N$ filter.

In some embodiments, the analyzing step further comprises quantizing the data of the image by dividing the data of the image in to M bins using a comb mask having M teeth and selecting for pixel data above a threshold in the data divided into M bins, wherein M is sufficiently high to cover the data of the image. In some embodiments, the analyzing step comprises reconstructing a three-dimensional profile from the data of the image.

In some embodiments, the analyzing step comprises converting the three-dimensional profile to a two-dimensional profile by transforming the three-dimensional profile to a local coordinate system. In some embodiments, the analyzing step comprises generating a feature vector by normalizing and concatenating the two-dimensional profile.

In some embodiments, the analyzing step comprises generating a pose vector by inputting the feature vector to a machine learning model, wherein the pose vector provides at least one of the location, orientation, and rotation of the object of interest in three dimensional space. In some embodiments, the selecting step uses a bitwise AND operator. In some embodiments, the reconstructing the three-dimensional profile comprises applying triangulation technique to the data of the image. In some embodiments, the feature vector comprises normalized and concatenated two-dimensional profiles generated from all segmented data of the image. In some embodiments, the machine learning model comprises a neural network. In some embodiments, the steps (a)-(e) are repeated during a surgical procedure.

Described herein are computer-based methods for tracking an object of interest comprising: (a) inputting data of an image comprising a light beam projected onto a contour of an object of interest into a software module using a processor; (b) applying a first set of predetermined number (N) of convolution filters to the data of the image to generate first filtered images and merging the first filtered images into a first merged image using the software module; (c) quantizing the data of the image by dividing the data of the image in to M bins using a comb mask having M teeth and selecting for pixel data above a threshold in the data divided into M bins using the software module; (d) reconstructing a three-dimensional profile from the image using the software module; (e) converting the three-dimensional profile to a two-dimensional profile using the software module; (f) generating a feature vector by normalizing and concatenating the two-dimensional profile using the software module; and (g) generating a pose vector by inputting the feature vector to a machine learning model, wherein the pose vector provides at least one of location, orientation, and rotation of the object of interest. In some embodiments, the method further comprises segmenting the data of the image into at least two segmented data of the image, wherein a number of segmented data is determined by a number of featured patterns of the light beam. In some embodiments, step (b) further comprises applying a second set of predetermined number (N) of convolution filters to the first merged image to generate the predetermined number (N) of second filtered images and merging the second filtered images into a second merged image. In some embodiments, the convolution filter comprises a two-dimensional convolution filter of D×D×1 dimension. In some embodiments, M of M teeth of the comb mask is sufficiently high to cover the data of the image. In some embodiments, the selecting for pixel data above a threshold in step (c) uses a bitwise AND operator. In some embodiments, the reconstructing the three-dimensional profile in step (d) comprises applying triangulation technique to the data of the image. In some embodiments, converting the three-dimensional profile to the two-dimensional profile in step (e) comprises transforming the three-dimensional profile to a local coordinate system. In some embodiments, the feature vector comprises normalized and concatenated two-dimensional profiles generated from all segmented data of the image.

In some embodiments, the machine learning model comprises a neural network. In some embodiments, the neural network comprises a convolutional neural network with fully connected layers for regression of the pose vector. In some embodiments, the machine learning model is trained. In some embodiments, the convolution filter is trained.

In some embodiments, the light beam from the light source passes through a patterned filter. In some embodiments, the patterned filter has a patterned slit in a crosshair shape and the light beam has a crosshair pattern. In some embodiments, the light beam from the source comprises one or more wavelengths.

In some embodiments, the object of interest comprises a body part of a subject. In some embodiments, the body part comprises bones of a joint. In some embodiments, the method occurs during a surgical procedure. In some embodiments, the steps (a)-(g) are repeated during a surgical procedure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 7A shows an algorithm workflow comprising convolving the image with a set of convolution filters and fusing the images by convolving with a filter to produce a final filtered image. FIG. 7B shows an algorithm workflow comprising convolving the image with a set of convolution filters to produce a set of filtered images, averaging the filtered images piecewise to produce a filtered image, and further fusing the filtered images by convolving with a filter to produce a final image.

FIG. 10 shows an example of a workflow to convert a three-dimensional profile to a two-dimensional profile by transforming the three-dimensional profile data into a local coordinate system.

FIG. 13 shows an exemplary embodiment of a method for markerless tracking and registering an object of interest.

DETAILED DESCRIPTION

Provided herein are devices, systems, and methods for a three-dimensional registering, tracking, and/or guiding an object of interest, such a body part, a surgical tool, or an implant, during a surgical procedure. Such devices, systems, and methods may offer minimally invasive, high precision registering, tracking, and/or guiding of the object of interest using a patterned light beam, including but not limited to a crosshair pattern, and data processing using artificial intelligence. The devices, systems, and methods disclosed herein may provide an accurate, real-time, three-dimensional surgical navigation for a system for robotic surgery or robotic-assisted surgery. This may improve the ability of the system for robotic surgery or robotic-assisted surgery to understand its operating room environment and the accuracy of the surgery performance. Such improvements may lead to shorter surgical time and better surgical outcome for the patient.

Figure 1A:
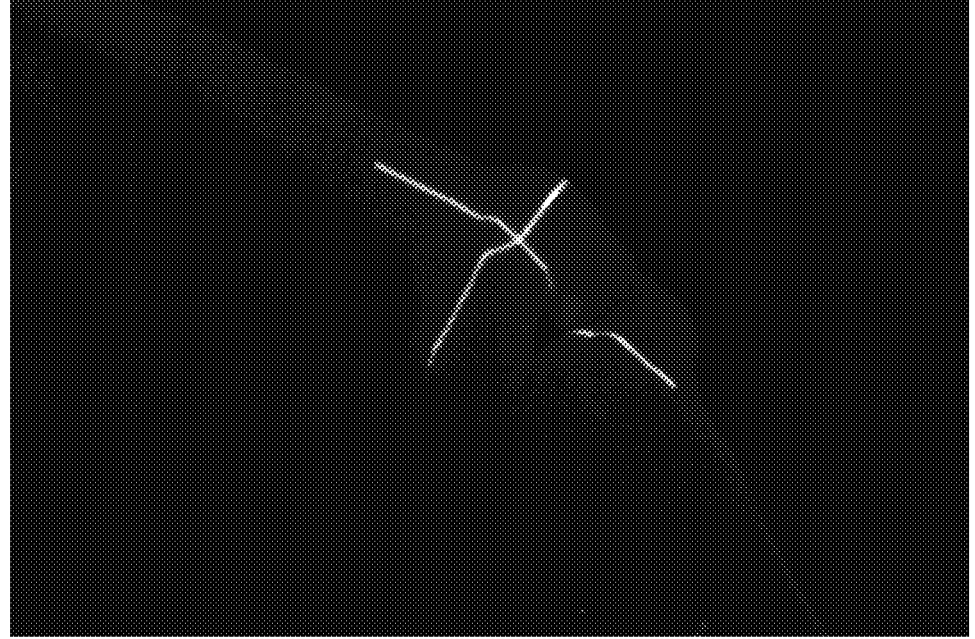
FIG. 1A shows an example of structured light used for the methods, devices, and systems described herein in place of cumbersome tracking arrays used in current robotic surgical systems.
Figure 1B:
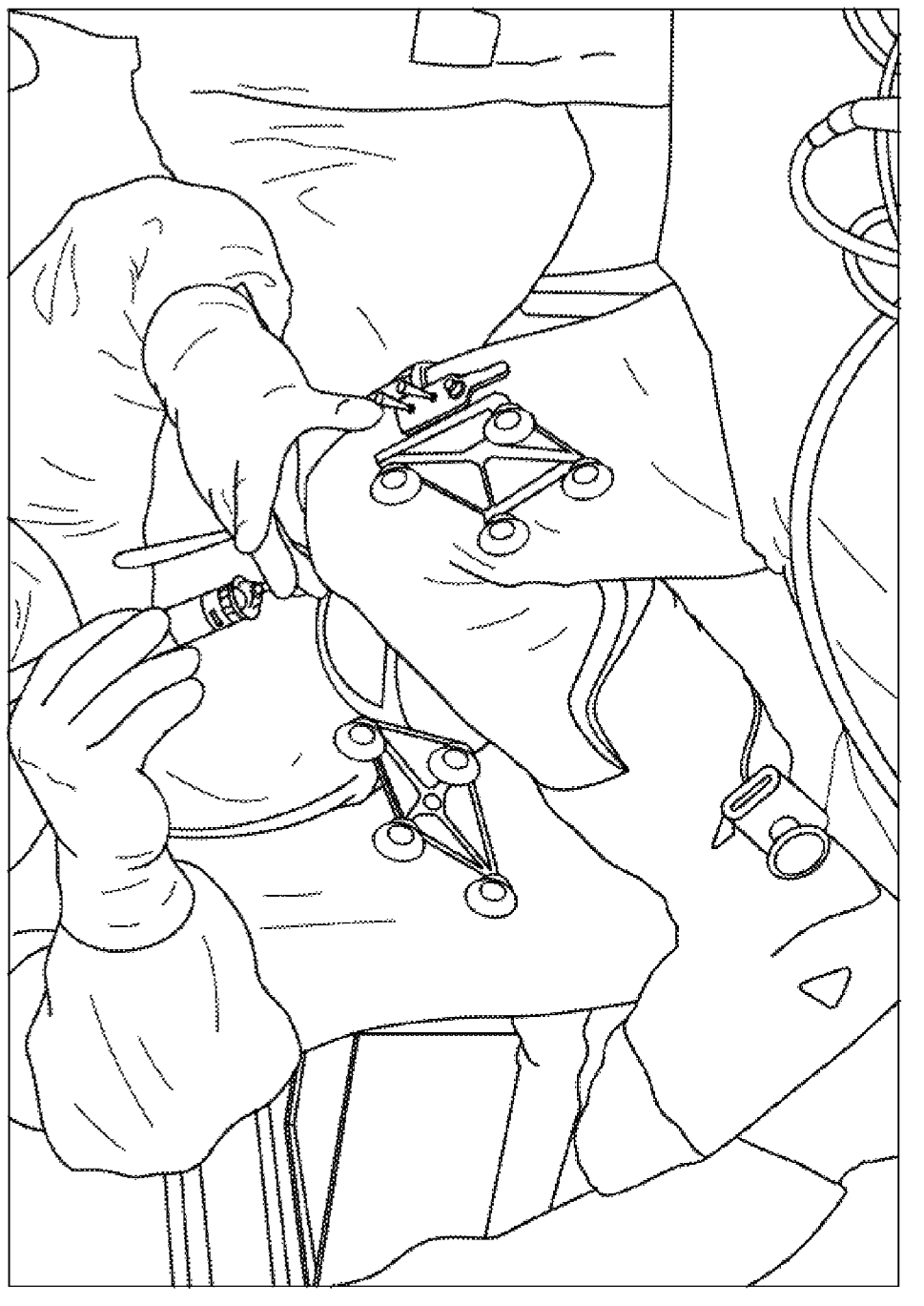
FIG. 1B shows an example of tracking arrays drilled into a patient's leg in a more invasive approach to tracking the patient's leg.

Disclosed herein are methods, devices, and systems for three-dimensional registering, tracking, and/or guiding of the object of interest without using a marker. Alternatively, the methods, devices, and systems disclosed herein may be compatible with a simple marker or markers placed by a minimally invasive method on the object of interest. The ability to register, track, and/or guide without large markers, which sometimes are drilled into place at or near the object of interest in the patient and/or protrude out from their placement site, can be valuable. The methods, devices, and systems described herein for registering, tracking, and/or guiding without a marker or with a simple marker may avoid an invasive procedure to place the marker and damage to tissue at and around the object of interest. Usually, robot-assisted surgical systems rely on a marker-based tracking and a triangulation approach to track tools and body parts. FIG. 1B shows an example of protruding marker arrays drilled into a patient's leg in an invasive procedure to track the patient's leg, which can cause tissue damage at and near the drilled sites and extend the surgical procedure time. Such invasive fixation of markers to bones may lead to complications, infections, nerve injury, and bone fracture and may reduce the flexibility during the procedure. Accordingly, the methods, devices, and systems described herein may require shorter surgical time as the additional time to invasively place the large markers is not needed. Often, a shorter surgical procedure time may result in better surgical outcomes and less complications for the patient.

Provided herein are methods, devices, and systems for minimally invasive, high precision, three-dimensional registering, tracking, and/or guiding of an object of interest during a surgical procedure to improve the performance of the surgery. The three-dimensional navigation based on the registering, tracking, and/or guidance may provide a real-time analysis of the body part to be operated on, such as the location, rotation, and orientation of bones of a joint in a total joint arthroplasty, which may aid the surgeon or health-care professional in their performance of the surgery. The three-dimensional navigation may be used to make recommendations, guidance, and/or instruction on the surgical procedure, such as a location for making a cut on a body part or a choice of an implant or a device to use in the surgical procedure. The three-dimensional navigation may be used to provide recommendations or instructions to a robotic or robotic-assisted surgery system in performing the surgery. The three-dimensional navigation may provide a more accurate recommendation or instructions than by eye of the healthcare professional or without the navigation. As such, methods, devices, and systems provided herein may result in improvement performance of the surgery by the healthcare professional or a robotic system.

The methods, devices, and systems described herein provide for registering and tracking an object of interest, such as a body part of a patient, and providing guidance to a surgeon or healthcare professional performing a surgical procedure during the surgical procedure. The devices and system may comprise a light source, an imaging module, and a processor having a software module and are interconnected to perform the methods described herein. Often, the methods, devices, and systems disclosed herein comprise steps of aiming a light beam from a light source at the object of interest, projecting the light beam onto a contour of the object of interest, obtaining an image of the light beam projected onto the contour of the object of interest using an imaging module, inputting data of the image into a software module for a processor, and analyzing the data of the image to determine at least one of orientation, rotation, and location of the object of interest in three-dimensional space using the software module. Usually, the light source, the imaging module, the processor, and the software module are interconnected and integrated into a system. Sometimes, the object of interest comprises more than one object, such as femur and tibia of a knee joint. Often, the light beam from the light source may pass through a patterned filter before being projected onto the object of interest. In some embodiments, the patterned filter has a patterned slit, and the resulting light beam has the pattern of the slit. In some embodiments, the pattern is a crosshair shape. In some embodiments, the patterned light beam provides a structured light that facilitates processing using artificial intelligence (AI) and machine learning (ML) for registering, tracking, and/or guiding.

In some embodiments, the information of orientation, rotation, and/or location of the object of interest is used to provide guidance and recommendation to the surgeon or healthcare professional performing a surgical procedure. In some embodiments, the guidance and recommendation are displayed on a screen with a graphic user interface. In some embodiments, the guidance and recommendation comprise how to perform at least one surgical step in a surgical procedure. In some embodiments, the guidance and recommendation comprise displaying where to make cuts for an osteotomy or a joint replacement or resurfacing. In some embodiments, guidance and recommendation comprise which joint replacement or resurfacing implant to use based on the dimension of the implant or where and/or how to place the implant in the joint of the patient. In some embodiments, the object of interest is imaged and analyzed throughout the surgical procedure using the methods, devices, and systems described herein.

Provided herein are methods, devices, and systems using AI and ML tracking and registering an object of interest and providing guidance to a surgeon during a surgical procedure. The methods, devices, and systems described herein comprise inputting data of an image comprising a light beam projected onto a contour of an object of interest into a software module using a processor; applying a convolution filter to the data of the image using the software module; quantizing the data of the image by dividing the data of the image into M bins using a comb mask having M teeth and selecting for pixel data above a threshold in the data divided into M bins using the software module; reconstructing a three-dimensional profile from the image using the software module; converting the three-dimensional profile to a two-dimensional profile using the software module; generating a feature vector by normalizing and concatenating the two-dimensional profile using the software module; and generating a pose vector by inputting the feature vector to a machine learning model, wherein the pose vector provides at least one of orientation, location, and rotation of the object of interest. In some case, the convolution filter comprises a set of convolution filters. In some cases, the convolution filter is applied to the image data to segment the image data into segments that are easier to analyze. In some cases, converting the three-dimensional profile to a two-dimensional profile comprises transforming the three-dimensional profile into a local coordinate system. In some cases, transformation into the local coordinate system reduces the dependency of the image data analysis on the location and orientation of the imaging module and allows for analysis irrespective of the location of the imaging module. In some cases, the pose vector is analyzed to provide guidance and recommendation for the surgeon or healthcare professional during the surgical procedure.

Markerless Navigation Device and System

Figure 2:
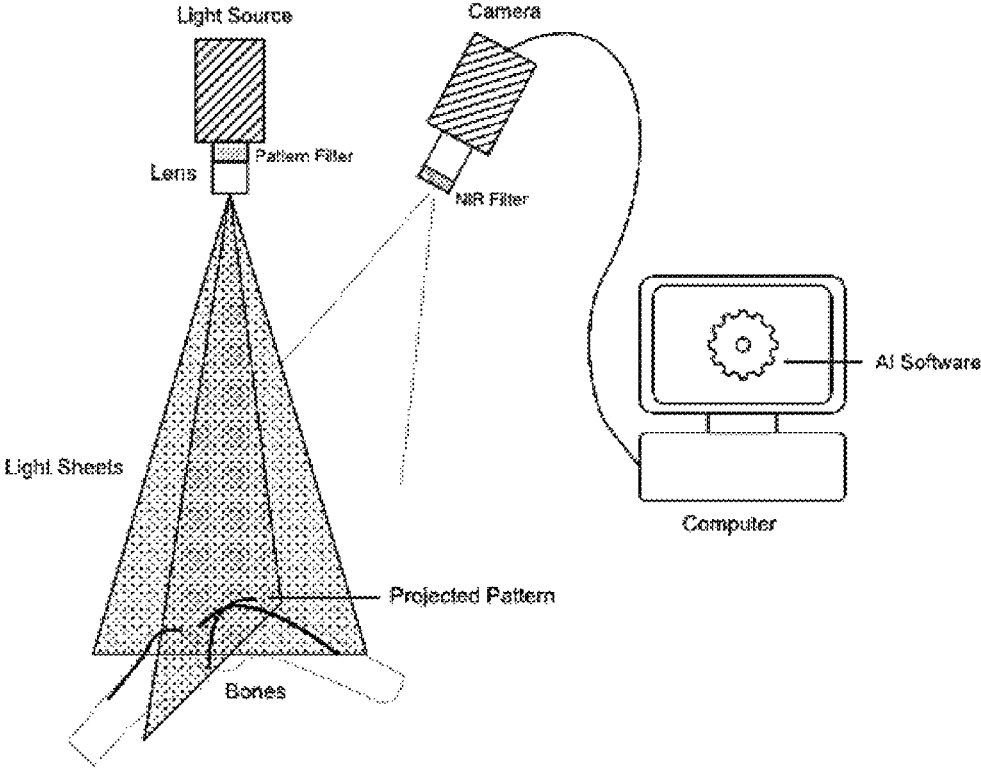
FIG. 2 shows an example of an overview of the system comprising a light source having a patterned filter and a lens, a camera, and a processor having an AI software for the navigation methods described herein.

The methods, devices, and systems provided herein comprise a light source, an imaging module, and a processor having a software module, and are interconnected and integrated to perform the methods described herein. FIG. 2 shows an example of an overview of the system comprising a light source having a patterned filter and a lens, a camera, and a processor having AI software for the navigation methods described herein.

In some embodiments, navigation by the methods, devices, and systems provided herein comprises at least one of registering, tracking, and guiding the object of interest. In some embodiments, the object of interest comprises a body part of the patient or a surgical tool or instrument. In some embodiments, the object of interest comprises a joint of the patient. In some embodiments, the object of interest comprises the bones of the joint. In some embodiments, the surgical tool or instrument may be a part of a robotic surgical system.

In some embodiments, registering comprises determining the position of the object of interest in comparison to a prior imaging or visualization of the object of interest. In some embodiments, prior imaging or visualization may include but is not limited to computer tomography (CT) scan, magnetic resonance imaging (MRI) scan, x-ray, positron emission tomography (PET), or ultrasound. In some embodiments, registering refers to relating one or more of the prior imaging or visualization to the location, orientation, and/or rotation of the object of interest generated by the methods, devices, system described herein. In some embodiments, the registration synchronizes the images and information obtained from various imaging modalities. The registration may facilitate the navigation of surgical instruments and tools by the robotic surgical system. In some embodiments, the registration facilitates recommendations of surgical steps provided by the methods, devices, and systems provided herein.

In some embodiments, tracking refers to following the location, rotation, and/or orientation of a body part or a surgical tool during a surgical procedure. In some embodiments, tracking comprises following the relative location, rotation, and/or orientation of a surgical tool to a body part during a surgical procedure. Usually, the surgical tool that is tracked during a surgical procedure is a part of the robotic surgical system. In some embodiments, tracking provides real-time information of location, rotation, and/or orientation of the body part or the surgical tool during the surgical procedure.

In some embodiments, location refers to a position of the object of interest in space. In some embodiments, location may be given in relation to an objective reference point. In some embodiments, orientation refers to relative position and/or direction of the object of interest. In some embodiments, orientation may be given in relation to a local coordinate to the object of interest. In some embodiments, rotation describes the movement of the object of interest about a point or an axis of rotation. In some embodiments, translation refers to movement of every point of the object of interest by the same distance in a given direction.

Light Source

Usually, the light source provides a light beam having a high-intensity radiance and a fixed wavelength. In some instances, the light source comprises a light-emitting diode (LED). In some instances, the light source comprises a laser. In some instances, the light source may be chosen based on light intensity or wavelength. In some instances, the light source emits a light beam at one wavelength. In some instances, the light source emits a light beam comprising at least two wavelengths. In some instances, the light source provides a light beam comprising wavelengths in the red, infrared, or green ranges. In some instances, the light source provides a light beam at least one of 530 nm (green), 625 nm (red), and 850 nm (infrared). In some instances, the light source provides a light beam having a wavelength in between about 900 nm to about 500 nm, about 900 nm to about 800 nm, about 700 nm to about 600 nm, or about 600 nm to about 500 nm.

Figure 3:
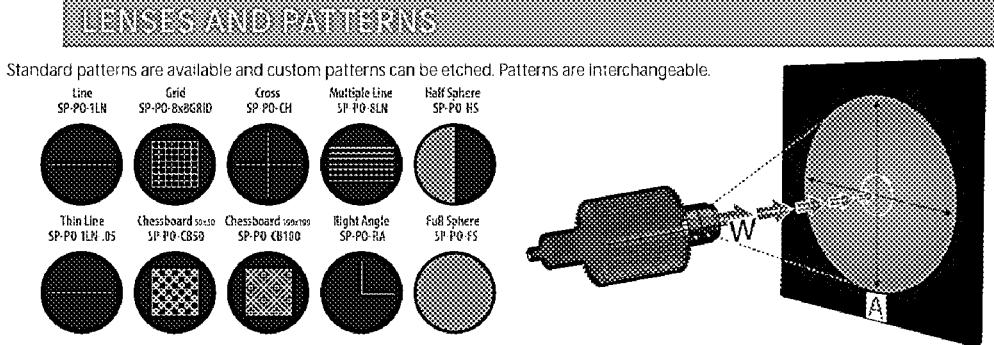
FIG. 3 shows examples of lenses and patterns that can be used for the filter for the light source.

Often, the light beam provided the light source may pass through a lens. In some cases, the lens comprises an optical lens. In some cases, the lens comprises a patterned filter. In some cases, the patterned filter may shape the light beam to a particular pattern. FIG. 3 illustrates examples of lenses and patterns that can be used for the filter for the light source. In some cases, the filter pattern maybe at least one of a line, a grid, a cross, multiple lines, a half sphere, a thin line, a chessboard, a right angle, or a full sphere. In some cases, the filter pattern is a cross, also referred herein as crosshair.

In some embodiments, the light beam is projected onto the object of interest. Usually, the light beam has a pattern that creates a unique projected pattern on the object of interest that can be used to identify the location, orientation, and/or rotation of the object. In some embodiments, the object of interest comprises at least two objects of interest that are tracked. In some embodiments, the object of interest comprises a plurality of objects of interest that are tracked. In some embodiments, the locations, orientations, and/or rotations of the plurality of objects can be tracked.

Imaging Module

The imaging module of the methods, devices, and systems provided herein is used to capture an image of the light beam projected onto the object of interest. In some instances, the imaging module comprise a camera. In some instances, the imaging module comprises a standard area scan camera. In some embodiments, the camera is a monochrome area scan camera. In some embodiments, the imaging module comprises a CMOS sensor. In some instances, the imaging module is selected for its pixel size, resolution, and/or speed. In some instances, pixel size and resolution affect the final tracking accuracy. In some instances, the camera speed (capturing and data transfer) determines the frame rate (latency). In some instances, the imaging module captures the images in compressed MPEG or uncompressed raw format. In some instances, the image comprises a data file in an image file format, including but not limited to JPEG, TIFF, or SVG. In some instances, the image comprises a data file in a video file format, including but not limited to MPEG or raw video format. In some instances, the image comprises video frames. In some instances, the imaging module is positioned and oriented at a different angle from the light source. In some instances, the imaging module is positioned and oriented to wholly capture the patterns projected on the object of interest. In some instances, the imaging module is configured to make the projected patterned light beam clearly visible and dim the rest of the environment, including the object. FIG. 1A shows an exemplary image of the crosshair-patterned projected light beam on the object captured by the imaging module. In some instances, images are captured by a standard area scan camera, which streams video frames in compressed MPEG or uncompressed raw format to a computer via an ethernet connection. In some instances, the captured image is transferred to a computer. In some instances, the image transfer to a computer occurs by an ethernet connection. In some instances, the image transfer to a computer occurs wirelessly, including but not limited to Wi-Fi or Bluetooth. In some instances, the power is supplied via Power-over-Ethernet protocol (PoE).

The imaging module may need to be calibrated prior to use. In some embodiments, the imaging module may be calibrated so that the imaging module is configured for use with complex light beam patterns. Some calibration methods generally work with a line, stripes or a grid and are not compatible with more complex patterns. Various methods of calibrating laser scanning systems often may rely on scanning a known object and recovering the relative poses of both the laser (e.g. light source) and the camera (e.g. imaging module). In some cases, scanning objects may require a conveyor system, which may be error-prone and time consuming. The calibration method may allow for a highly accurate, simpler, and easier to implement calibration approach.

Image Processing Workflow

Figure 4:
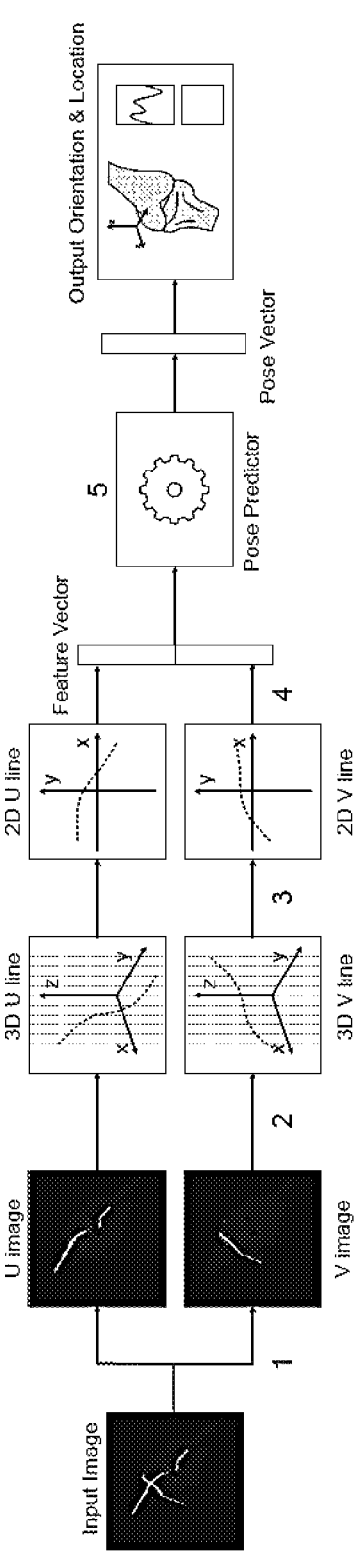
FIG. 4 shows an example of a processing workflow for an exemplary navigation system. The raw image of an object of interest is taken from the camera and input into the navigation system. The image is segmented into two images, sampled for pixels above a threshold, converted into three-dimensional lines, transformed into a two-dimensional point cloud in a local coordinate system, concatenated into a feature vector, and converted into a pose vector by the system. The pose vector comprises information about the position, rotation, translation, and/or orientation of the object of interest. The system can output a visualization of the object of interest in the current state.

The image taken by the imaging module may be inputted into a computer comprising a software module and a processor. FIG. 4 illustrates an exemplary workflow of image data processing, where the system takes the images from the imaging module as an input and outputs the orientations and locations of the objects within the image. The input image may be segmented into at least two images, one for each leg of the crosshair, referred herein as U and V image. The segmented U and V images may be quantized by sampling bright pixels in the images. The quantized images may be converted to three-dimensional lines by using triangulation techniques. The three-dimensional points may be transformed into local coordinate systems of light sheets from the crosshair patterned light beam to obtain a two-dimensional point cloud. These two-dimensional point cloud points may be concatenated to form a feature vector, which can be input into a pose predictor. The pose predictor can predict a pose vector, representing location, rotations, and/or translations of the object of interest. The object of interest may be visualized in its current state.

Figure 5:
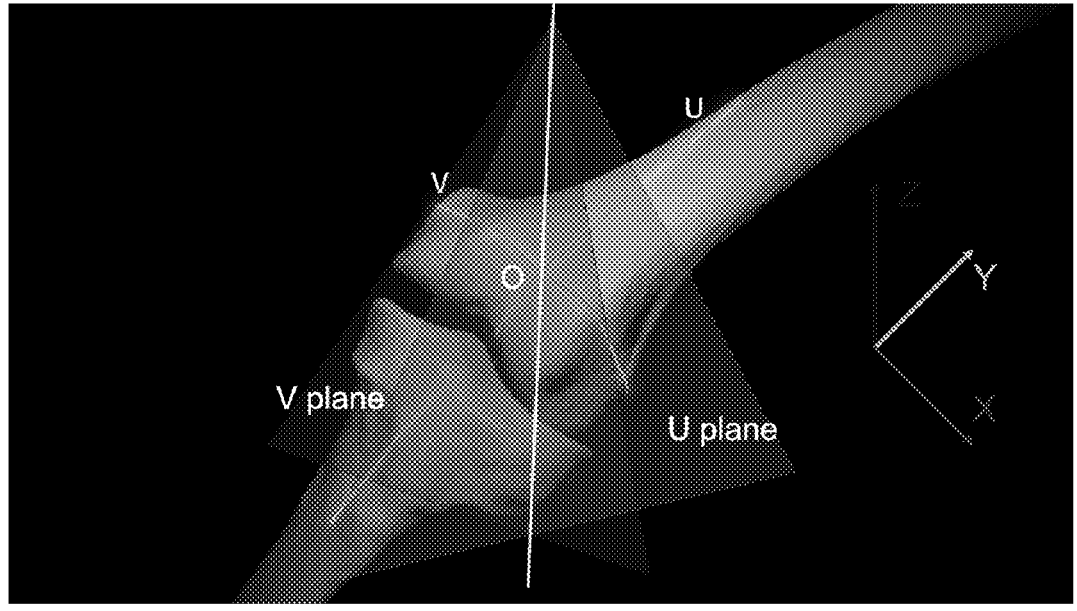
FIG. 5 shows an example of a crosshair-patterned light beam projected onto a knee joint along with two planes of light sheets that intersect each other in a central ray, that is shown in yellow.

In some embodiments, when the light beam has a crosshair-pattern, the two legs of the crosshair may be referred to as "U" and "V" and the 2 planes defined by the light sheets as U plane and V plane respectively. In some embodiments, the intersection of the two planes is referred herein as the central ray, which shown in yellow or light gray in FIG. 5. In some embodiments, in the context of knee joint tracking, the U line may span the femur and the tibia in near vertical directions and the V line may cut either femur or tibia horizontally as shown in FIG. 5.

Image Segmentation

Figure 6:
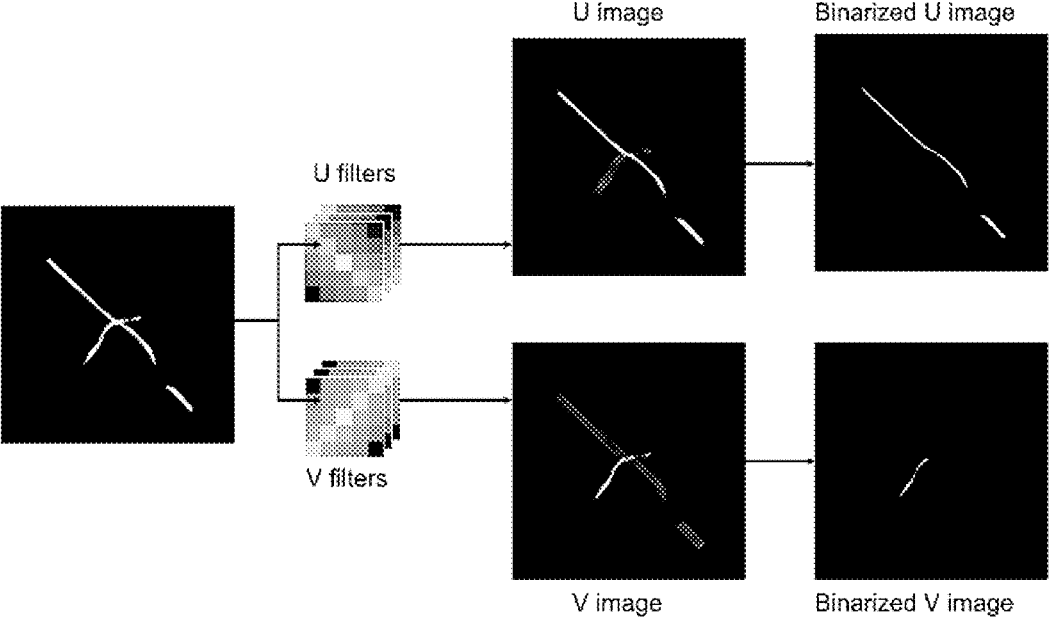
FIG. 6 shows an example of segmentation of an image comprising a crosshair-patterned light beam projected onto the object of interest with U and V filters. The image of the light beam projected onto the object of interest is processed by thresholding, blurring, and segmenting into light beam pattern components, represented as U image and V image, by convolving with a set of two-dimensional filters.

Usually, the image may be segmented to capture the salient features of the unique pattern of the projected light beam on the object of interest. In some embodiments, the image may be segmented to simplify the image and to make the image data easier to analyze in subsequent steps. An exemplary workflow for image segmentation by convolution is shown in FIG. 6. In an image segmentation workflow, the images may be preprocessed by thresholding followed by blurring. In some cases, the image may be segmented by convolving it with at least one set of convolution filters. In some cases, the image may be segmented by convolving it with multiple sets of convolution filters at different stages of the workflow. In some embodiments, the convolution filters are two-dimensional filters. In some embodiments, the convolution filters are a set (N) of $D \times D \times 1$ filters. In some embodiments, the image may be segmented by partitioning the image into different groups focused on different features of the image, including but not limited to the features that help identify an object in the image or boundaries of the object in the image. In some embodiments, the image may be segmented into a plurality of images. In some embodiments, the image may be segmented into at least two images. In some embodiments, the input image having a crosshair pattern may be segmented into two images, each image corresponding to one of the legs of the crosshair. In some embodiments, the segmented images corresponding to each leg of the crosshair are referred to as U and V images. In some embodiments, the segmentation uses a threshold-based approach using a single threshold or multiple thresholds. In some embodiments, the segmentation uses an edge-based approach to detect the edges in the input image. In some embodiments, the segmentation uses a region-based approach to detect region boundaries in the input image.

Figure 7A:
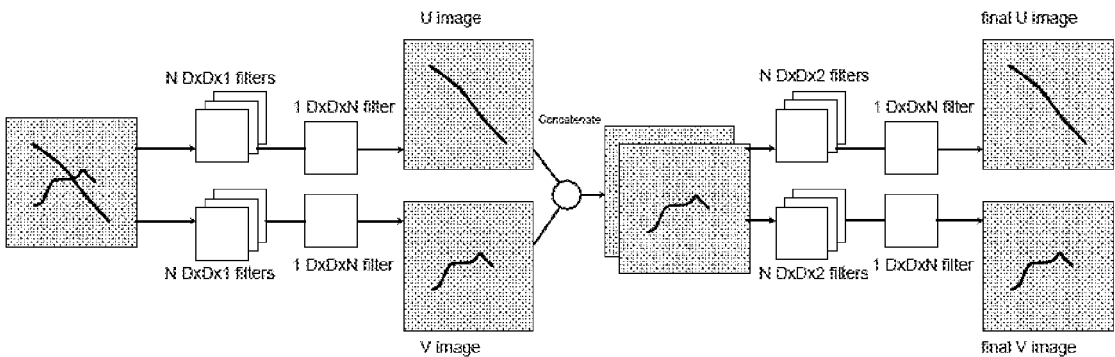
FIGS. 7A and 7B show two examples of filtering algorithms for crosshair segmentation.
Figure 7B:
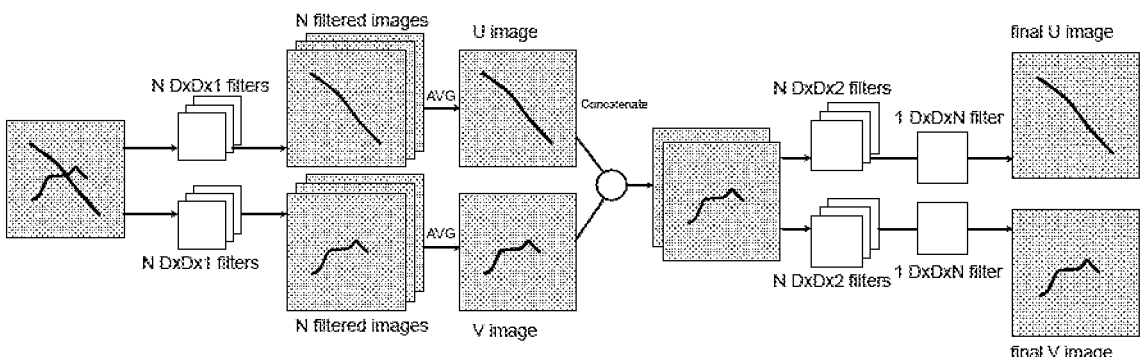

In some embodiments, one of the segmentation algorithms, as shown in FIGS. 7A and 7B, may be used. As shown in FIG. 7A, a convolutional architecture similar to that of a standard convolutional neural network (CNN) may be used to segment the image. In some embodiments, the image may be convolved with a first set (N) of first two-dimensional $D \times D \times 1$ convolution filters, producing N filtered images. In some embodiments, the N filtered images are then convolved with one $D \times D \times N$ filter to merge the N filtered images together to produce an intermediate filtered image. This process is performed for each segmented image that is generated. In some embodiments, the process described in FIG. 7A is repeated for U and V image separately for the image of the crosshair patterned light beam projected on to the object of interest. In some embodiments, the intermediate filtered images are concatenated to form an image with two channels. The intermediate filtered images are also referred herein as first merged images. In some embodiments, the merged image is convolved with a subsequent set of N second convolution filters having a dimension of $D \times D \times 2$ and followed by a $D \times D \times N$ filter in a second stage. In some embodiments, the weights of the filters are learned in a supervised manner with a dataset of input and output images. In some embodiments, the workflow undergoes training using a training dataset of input and output images to calculate the weights of the filters. In some embodiments, multiple convolution layers are applied to the image. In some embodiments, the first set of convolution filters and the subsequent set of convolutions filters may have the same dimensions or different dimensions.

FIG. 7B shows a segmentation algorithm using a convolutional architecture. In some embodiments, the image may be convolved with a first set (N) of two-dimensional $D \times D \times 1$ filters to produce N filtered images. In some embodiments, the filtered images may be averaged piecewise to produce the filtered image. In some embodiments, the filtered image comprises the segmented image. This process is performed for each segmented image that is generated. In some embodiments, the process described in FIG. 7B is repeated for U and V image separately for the image of the crosshair patterned light beam projected on to the object of interest. The segmentation algorithm as shown in FIG. 7B produces two intermediate filtered images. The intermediate filtered images are also referred herein as first merged images. In some embodiments, the intermediate filtered images are concatenated to form an image with two channels. In some embodiments, the merged image is convolved with a subsequent set of N D×D×2 filters and followed by a D×D×N filter in a second stage. In some embodiments, multiple convolution layers are applied to the image. In some embodiments, the first set of convolution filters and the subsequent set of convolutions filters may have the same dimensions or different dimensions.

The convolution filters used for methods and systems described herein and as shown in FIGS. 7A and 7B may have a variety of dimensions. In some embodiments, D is determined by the thickness of the projected light beam in the image. In some embodiments, D is 1, 2, 3, 4, 5, 6, 7, 8, 9, 10, 11, 12, 13, 14, 15, 16, 17, 18, 19, or 20. In some embodiments, D is at least 1, 2, 3, 4, 5, 6, 7, 8, 9, 10, 11, 12, 13, 14, 15, 16, 17, 18, 19, or 20. In some embodiments, D is at no more than 1, 2, 3, 4, 5, 6, 7, 8, 9, 10, 11, 12, 13, 14, 15, 16, 17, 18, 19, or 20. In some embodiments, N is 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100. In some embodiments, D is 5. In some embodiments, N is at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100. In some embodiments, N is no more than 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100.

In some embodiments, the parameters of the filter are learned in a supervised manner. In some embodiments, the training dataset may be built by collecting a small number of image frames containing the light beam pattern of interest, such as the crosshair pattern, at various poses of object of interest. In some embodiments, the training dataset may be built by collecting a small number of image frames containing the crosshair light beam at various poses of the femur and tibia or various bones of a joint. In some embodiments, the original image may be segmented using an image editing software. In some embodiments, the segmented images comprise U and V images that are segmented using an image editing software. In some embodiments, pairs of input-output data (input_image, output_u,output_v) are used to train the filters in a supervised fashion. In some embodiments, the training is performed using automatic differentiation and adaptive optimization approaches. In some embodiments, Tensorflow 2.0 with Adam optimizer may be used to train the filters using the training dataset.

Image Quantitation and Three-Dimensional Reconstruction

The segmented images from the original image may be quantized and converted into a three-dimensional profile to prepare the image data for further processing to determine location, orientation, and/rotation information of the object of interest. In some embodiments, the image is quantized to compress the image in size. The smaller image file size facilitates faster processing and easier handling of the image by the processor. In some embodiments, each of the segmented images is quantized and converted to a three-dimensional profile. In some embodiments, some of the segmented image are quantized and converted to a three-dimensional profile. Sometimes, quantization comprises applying a comb mask to the segmented image to divide up image into sections, selecting for bright pixels above a threshold within a divided segmented image section, and averaging the bright pixel clusters in the section. In some embodiments, the segmented images are quantized by applying a bitwise operator on the segmented image and a template image. The resulting quantized image comprises one or more pixel clusters. In some embodiments, the resulting quantized image comprises a plurality of pixel clusters. In some embodiments, the mean of each pixel cluster is calculated to generate a list of two-dimensional image points. In some embodiments, the list of two-dimensional image points can be converted to three-dimensional points. In some embodiments, a triangulation technique is used to convert the two-dimensional image points to three-dimensional points. In some embodiments, the segmented U and V images are quantized by applying a bitwise AND operator on the segmented U and V images and a template image.

In some embodiments, the template image comprises a comb mask. In some embodiments, the comb mask is generated by projecting a three-dimensional comb in the image plane. In some embodiments, the comb mask is generated beforehand the quantization step. In some embodiments, the comb mask comprises a plurality of teeth. In some embodiments, the teeth of the comb mask are chosen to be reasonably large to cover the variations of the light beam pattern projected on to the object of interest. In some embodiments, the teeth of the comb mask may be reasonably large to cover the variations of the crosshair-patterned light beam projected on to the object of interest. In some embodiments, the comb mask comprises at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 teeth. In some embodiments, the comb mask comprises no more than 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 teeth. In some embodiments, the comb mask comprises 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 teeth.

In some embodiments, the bitwise operator comprises at least one of a bitwise AND operator, bitwise OR operator, bitwise NOT operator, bitwise XOR operator, bitwise complement operator, bitwise shift left operator, or bitwise shift right operator. In some embodiments, the bitwise operator comprises bitwise AND operator. In some embodiments, the bitwise AND operator selects for bright pixels that belong to a comb mask section, where the bright pixels have values above a threshold. In some embodiments, the comb mask section may coincide with a light plane, also referred herein as a light sheet. In some embodiments, the comb mask section refers to a section of the segmented image divided by the teeth of the comb mask. In some embodiments, the comb mask section is also referred to as regular comb. In some embodiments, the bitwise AND operator selecting for bright pixels in the comb section results in a quantized version of the segmented image. In some embodiments, the threshold is predetermined. In some embodiments, the threshold is adjusted for each individual image. In some embodiments, the threshold is a percentage of the brightest pixel in the image. In some embodiments, the threshold is at least about 20%, 30%, 40%, 50%, 60%, 70%, 80%, or 90% of the brightest pixel in the image. In some embodiments, the threshold is no more than about 20%, 30%, 40%, 50%, 60%, 70%, 80%, 90%, or 100% of the brightest pixel in the image. In some embodiments, the threshold is 20%, 30%, 40%, 50%, 60%, 70%, 80%, or 90% of the brightest pixel in the image.

Figure 8:
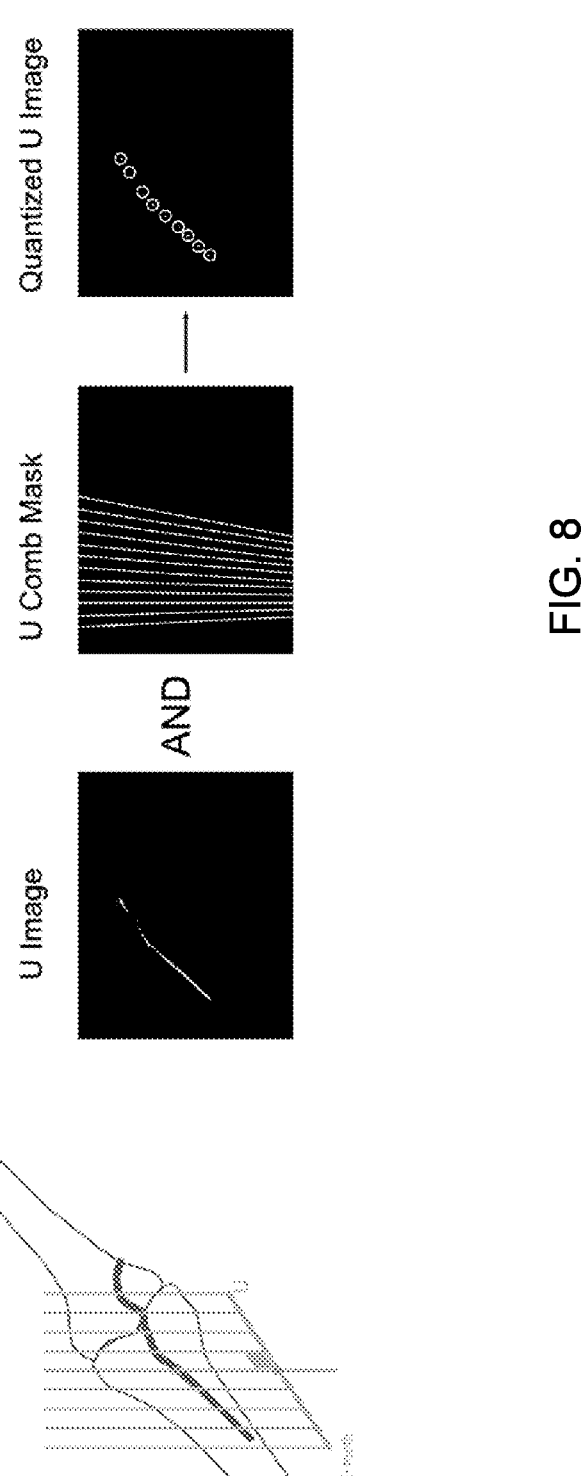
FIG. 8 shows an example of quantizing the pixels of a segmented image by a combing technique, where the segmented image is divided into sections by a comb mask and the bright pixels above a threshold are selected.
Figure 9:
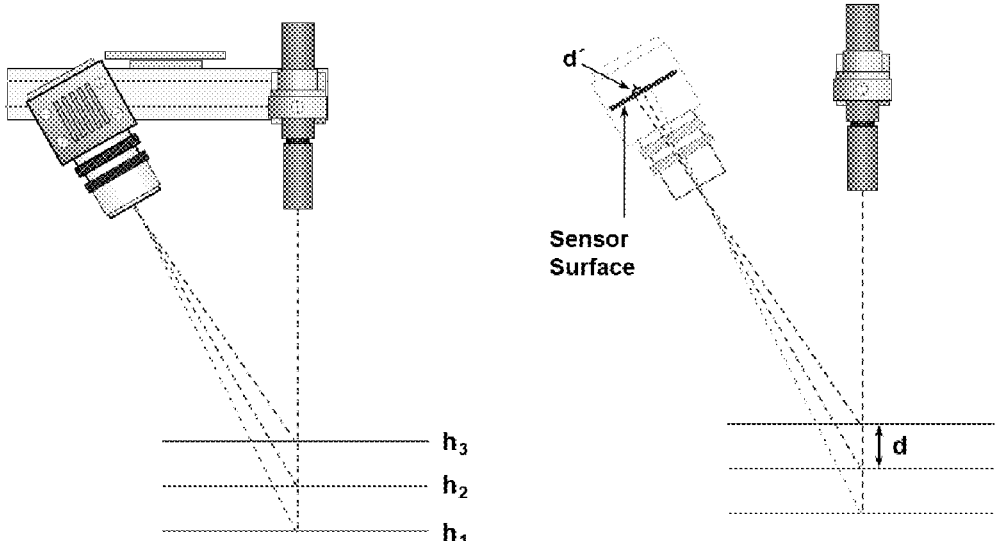
FIG. 9 shows an example of a standard triangulation method, which can be used to reconstruct a three-dimensional point cloud from a two-dimensional point cloud.

FIG. 8 shows an exemplary workflow for image quantization. The workflow starts with generating a comb mask by projecting a three-dimensional comb on the image plane, shown as green vertical lines along the femur and tibia of a joint in FIG. 8. The workflow comprises taking the segmented U image, applying a template image, which is shown as a U comb mask in FIG. 8, and applying AND operator to select the bright pixels that belong to a regular comb, which coincides with a light plane. This results in a quantized version of the segmented image comprising multiple pixel clusters. Usually, the mean of each pixel cluster may be calculated to generate a list of two-dimensional image points. A triangulation technique may be used to convert the two-dimensional image points to three-dimensional points. FIG. 9 shows an example of the standard triangulation technique that may be used to convert the two-dimensional image points to three-dimensional points.

Converting Three-Dimensional Profiles to Two-Dimensional Profiles

The reconstructed three-dimensional points, also referred herein as a three-dimensional profile, may be converted to a two-dimensional profile by transforming the reconstructed three-dimensional points to a local coordinate system. The transformation of the three-dimensional points to a local coordinate system can remove the dependency of the reconstructed three-dimensional points on the location and orientation of the imaging module. In some embodiments, the transformation allows for the imaging module to be flexible and not fixed to an operating room or a location. In some embodiments, the transformation allows for the imaging module to be repositioned during a surgical procedure or in between procedures and still allow the images taken after repositioning to be compared to the images taken prior to repositioning of the imaging module. In some embodiments, the transformation to a local coordinate system allows for image data taken at different times by the imaging module that was repositioned to be compared to each other.

In some embodiments, the reconstructed three-dimensional profile is converted to a two-dimensional profile by transforming them to a local coordinate system. In some embodiments, the conversion is performed for all of the three-dimensional profiles generated from quantization and three-dimensional reconstruction. In some embodiments, the conversion is performed for some of the three-dimensional profiles generated from quantization and three-dimensional reconstruction. In some embodiments, the local coordinate system is determined by the corresponding light sheets, also referred herein as light planes formed by the light beam projected on to the object of interest. In some embodiments, the local coordinate system is set in spatial relation to the light beam projected on to the object of interest. In some embodiments, the local coordinate system is set such that each of the two-dimensional profiles are connected to each other.

The left panel A of FIG. 10 shows an exemplary image of the patterned light beam projected onto a knee joint. The middle panel B of FIG. 10 shows a local coordinate system determined by the V light sheet, shown by a dashed triangle. In some embodiments, the local coordinate system is defined by 3 basis vectors, Ox, Oy and Oz. In some embodiments, Oz coincides with the central ray, or the intersection of two light sheets. In some embodiments, Oy belongs to the V plane, defined by V light sheet, and is perpendicular to Oz. In some embodiments, Ox is orthogonal to the Oxy plane and belongs to the U plane that is defined by U light sheet. In some embodiments, the exact location of O is chosen according to the actual setup. In some embodiments, the exact location of O may be a point on a physical surface, including but not limited to a table top, an operating table, or a fixed object. The right panel C of FIG. 10 shows exemplary two-dimensional profiles.

Forming Feature Vector from Two-Dimensional Profiles

Usually, the transformed two-dimensional profiles using local coordinate systems are normalized and concatenated to form a single feature vector. In some embodiments, each of the transformed two-dimensional profiles are normalized and concatenated. In some embodiments, concatenation converts the two-dimensional profiles into a single one-dimensional vector, also referred to as a string vector. In some embodiments, the concatenation reduces the dimension of the image data to facilitate the downstream processing steps. In some embodiments, the feature vector may be used as input to machine learning models in downstream steps. In some embodiments, the normalization of the concatenation of the two-dimensional profiles facilitates handling of the feature vector $f$ by the downstream machine learning steps.

In some embodiments, the transformed two-dimensional profiles may be written as ordered sets of y and z coordinates $C_u$ and $C_v$ as follows: $C_u = \{u_y^i, u_z^i\}$, $C_v = \{v_y^i, v_z^i\}$, $i \in [1, N]$, where N is the number of teeth in the comb mask from segmentation step. In some embodiments, the two-dimensional profiles comprise U and V two-dimensional profiles. In some embodiments, the feature vector may be formed by dropping the y-coordinates and concatenating $C_u$, $C_v$ and normalizing the concatenated vector as follows: $f = [u_z^1, \ldots, u_z^N, v_z^1, \ldots, v_z^N]/\lambda$, where $\lambda$ is a normalizing constant. In some embodiments, the values in vector $f$ is normalized to the [0,1] range. In some embodiments, $\lambda$ is the highest value in the two-dimensional profiles. In some embodiments, $\lambda$ is at least 1, 2, 3, 4, 5, 6, 7, 8, 9, or 10 times the highest value in the two-dimensional profiles. In some embodiments, $\lambda$ is a normalizing vector. In some embodiments, $\lambda$ vector has the same length as the feature vector.

Predicting Object Poses with Machine Learning

The feature vector $f$ may be input into a machine learning (ML) model that outputs a pose vector of the object of interest. The pose vector comprises information about the object of interest, including but not limited to position, location, rotation, and/or orientation of the object of interest. In some embodiments, the machine learning model (ML Model) takes the feature vector $f$ as input and outputs the pose vector of the object of interest.

In some embodiments, the pose vector comprises information on rotations and locations of the bones of a joint. In some embodiments, the pose vector represents rotations and locations of the femur and the tibia in the context of knee joint tracking. In some embodiments, the pose vector comprises a 14-element vector to represent the poses of the bones with a portion of the vector comprising information on rotation and location of each bone. In some embodiments, the pose vector comprises a 14-element vector to represent the poses of the femur and the tibia as follows:

$$P = [q_x^f, q_y^f, q_z^f, q_w^f, l_x^f, l_y^f, l_z^f, q_x^t, q_y^t, q_z^t, q_w^t, l_x^t, l_y^t, l_z^t],$$

where $$q^f = [q_x^f, q_y^f, q_z^f, q_w^f]$$

is femoral rotations in quaternion representation, $$l = [l_x^f, l_y^f, l_z^f]$$

is the normalized location of femur $$q^t = [q_x^t, q_y^t, q_z^t, q_w^t]$$

is tibial rotations in quaternion representation, and $$l = [l_x^t, l_y^t, l_z^t]$$

is the normalized location of tibia. In some embodiments, the relationship between the feature vector $f$ and pose vector P may be described as P=G($f$), where G comprises a neural network for pose prediction. In some embodiments, the neural network for pose prediction comprises an one-dimensional convolutional neural network having additional fully connected layers for regression of the pose vector. In some embodiments, the neural network for pose prediction comprises a multilayer perceptron.

Figure 12A:
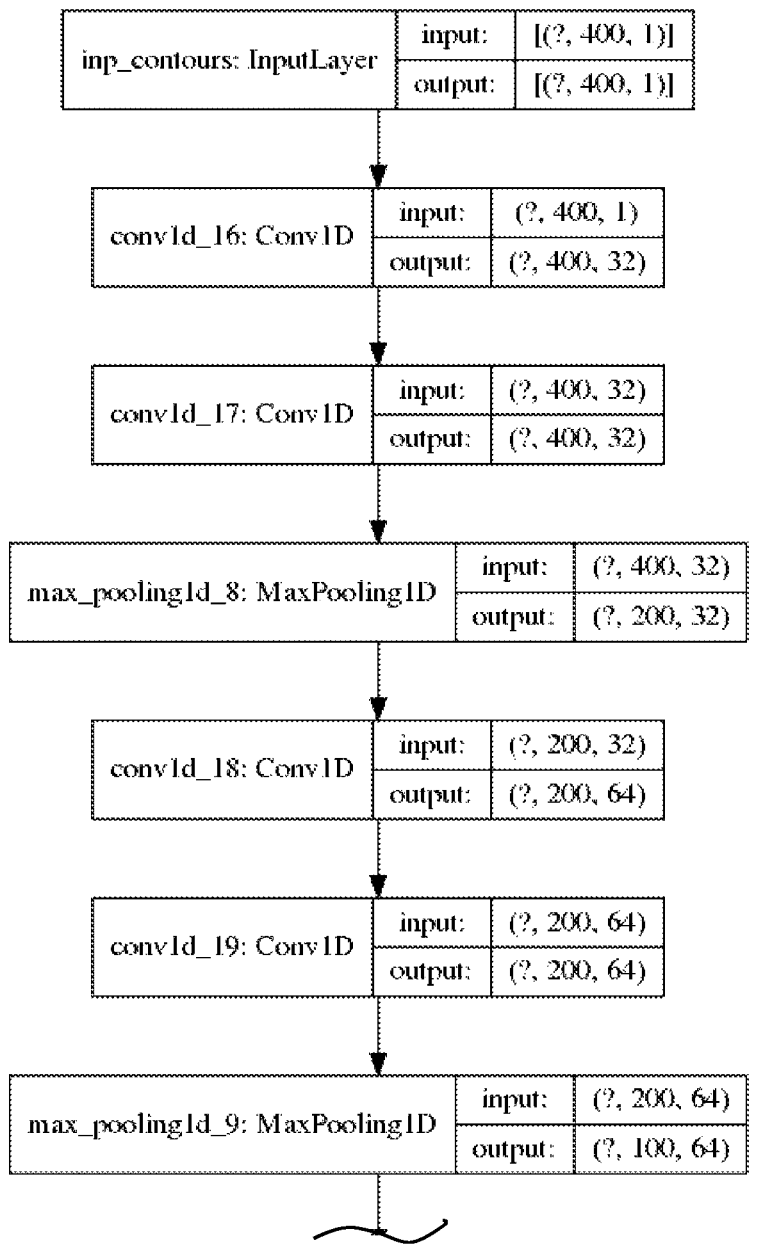
FIGS. 12A and 12B show an example of an architecture of a pose prediction neural network. The steps of FIG. 12A continues through FIG. 12B.
Figure 12B:
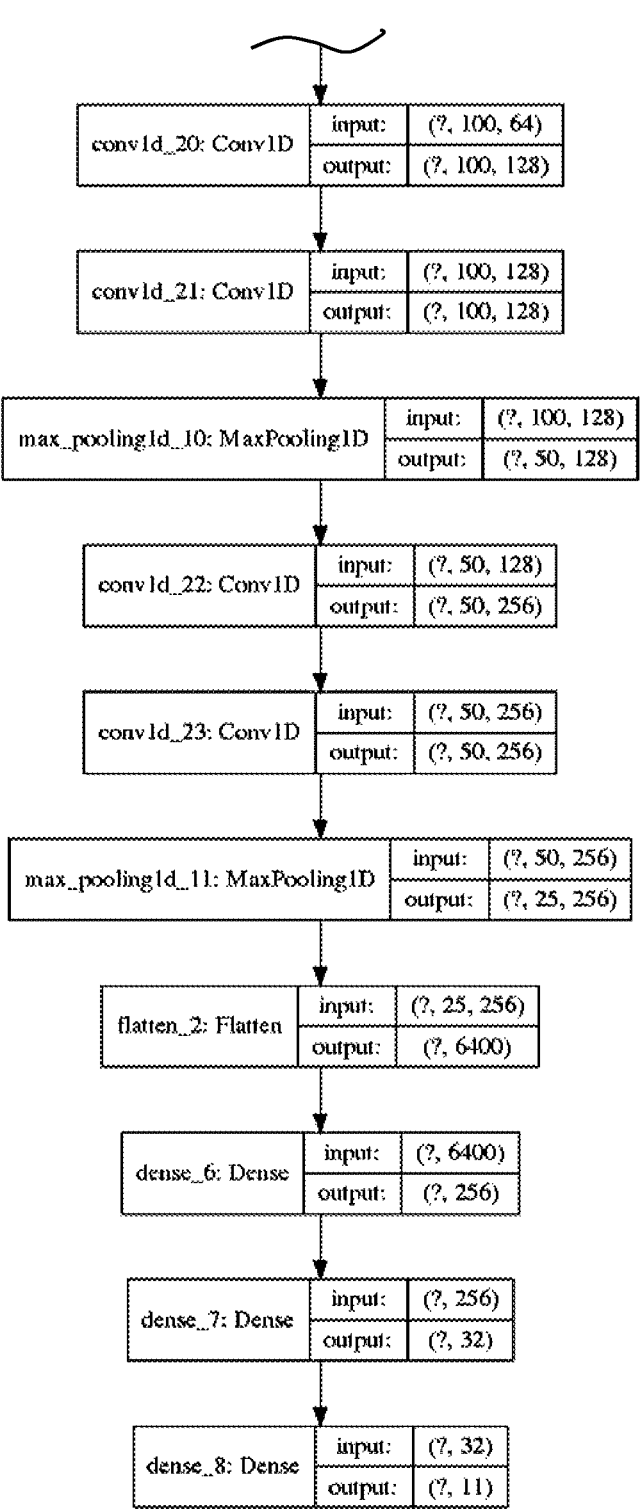

In some embodiments, FIGS. 12A and 12B provide an exemplary architecture of a neural network for pose prediction. The design of the network may follow best practices such as interleaving convolution layers with max-pooling layers to simplify network complexity and improve robustness. In some embodiments, two convolution layers are followed by a max-pooling layer as shown in FIGS. 12A and 12B. In some embodiments, 1, 2, 3, 4, 5, 6, 7, 8, 9, or 10 convolution layers are followed by a max-pooling layer. In some embodiments, at least 1, 2, 3, 4, 5, 6, 7, 8, 9, or 10 convolution layers are followed by a max-pooling layer. In some embodiments, no more than 1, 2, 3, 4, 5, 6, 7, 8, 9, or 10 convolution layers are followed by a max-pooling layer. In some embodiments, each subsequent layer has a higher number of filters than previous layer to account for different characteristics of the data at different scales. In some embodiments, the number of filters increases by a factor of 2. In some embodiments, techniques including but not limited to dilational convolution, strided convolution, or depth-wise convocation may be used to further improve performance and latency.

Figure 11:
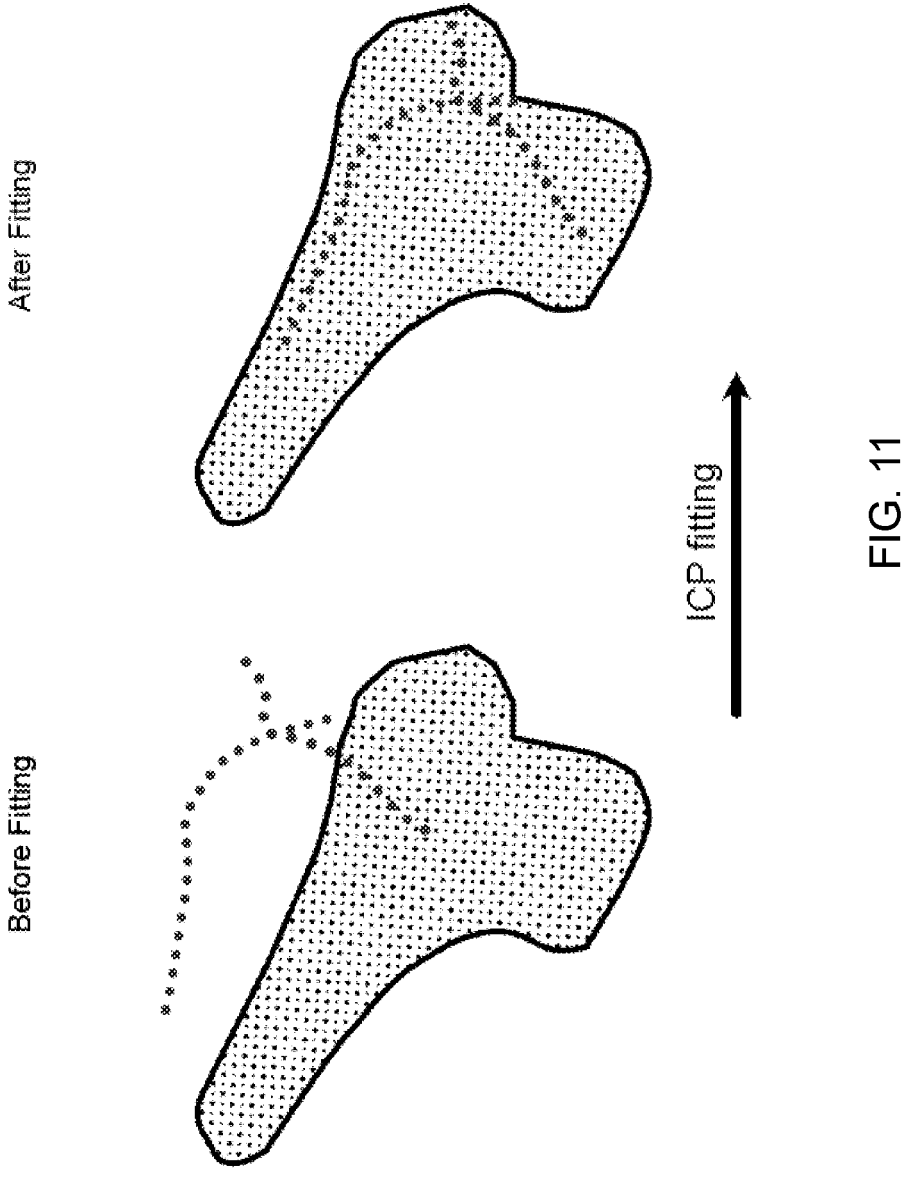
FIG. 11 shows an example of applying the iterative closest point (ICP) algorithm to register the crosshair point cloud with a bone model. Orange points belong to the crosshair.

In some embodiments, the pose vector of the object of interest may be used to provide a three-dimensional visual representation of the object of interest on a display. In some embodiments, initial location and rotation of the object of interest may be taken from the output of the machine learning model. In some embodiments, the poses of the bones may be refined further by applying a point cloud fitting method. In some embodiments, the point cloud fitting method comprises such an iterative closest point (ICP) algorithm. In some embodiments, the point cloud fitting method is applied to register the light beam pattern point cloud on a three-dimensional model of the object of interest. In some embodiments, the ICP algorithm may be applied to register the crosshair point cloud and a three-dimensional model of the corresponding bones as shown in FIG. 11. In some embodiments, the three-dimensional model of the object of interest comprises a computer-aided design (CAD) model. In some embodiments, the application of the point cloud fitting method results in full registration of the light beam pattern and the object of interest together. In some embodiments, the application of the ICP algorithm results in full registration of the crosshair and the bones together.

In some embodiments, the pose vector of the object of interest may be used to provide a three-dimensional visual representation of the object of interest on a display. In some embodiments, the visual representation of the object of interest may be manipulated by a user, such as rotating, zooming in, or moving the visual representation. In some embodiments, the visual representation of the object of interest may have recommendations on steps of the surgical procedure. In some embodiments, the recommendation comprises location and orientation of a cut to make on a bone for an arthroplasty or an orthopedic procedure.

The ML algorithm for pose prediction may be trained. In some embodiments, the ML algorithm for pose prediction is trained with a training dataset. In some embodiments, a synthetic training dataset is used to train the pose prediction neural network. In some embodiments, the ML algorithm for pose prediction is trained with an experimental dataset or a real dataset. In some embodiments, the images of light beam pattern, such as the crosshair pattern, may be generated using software such as Blender and Unity. In some embodiments, ground-truth pose vectors may be used to train the neural network. In some embodiments, data augmentation may be used to simulate real-world distortions and noises. In some embodiments, a training set comprising augmented data simulating distortion and noises is used to train the pose prediction neural network. In some embodiments, the pose prediction neural network is trained using automatic differentiation and adaptive optimization. In some embodiments, Tensorflow 2.0 with Adam optimizer may be used to train the pose prediction neural network.

FIG. 13 shows an exemplary embodiment of a method 1300 for markerless tracking and registering an object of interest. In step 1302, a light beam is projected onto a contour of an object of interest. In step 1304, an image of the light beam projected onto the contour of the object is obtained using an imaging module. In step 1306, the image is input into a software module for a processor. In step 1308, the image is segmented by applying convolution filters into segmented images. In step 1310, the segmented images are quantized and 3D profiles are reconstructed from the quantized images. In step 1312, the reconstructed 3D profiles are converted to 2D profiles by transformation to a local coordinate system. In step 1314, a feature vector is formed from the 2D profiles by concatenation and normalization. In step 1316, object poses are predicted by applying machine learning to the feature vector.

In some embodiments, the computer program is further configured to cause the processor to identify the location, orientation, and/or rotation of the object of interest within the image. In some embodiments, the orientation and/or rotation of the object of interest is expressed as an angle. In some embodiments, the location, orientation, and/or rotation of the object of interest frame is expressed as a distance, a ratio, a code, or a function.

In some embodiments, the imaging module captures the object of interest within the frame. In some embodiments, the object of interest comprises a joint of an individual. In some embodiments, the joint comprises at least one of a knee joint, a hip joint, an ankle joint, a hand joint, an elbow joint, a wrist joint, an axillary articulation, a stemoclavicular joint, a vertebral articulation, a temporomandibular joint, and articulations of a foot. In some embodiments, the joint comprises at least one of joint of a shoulder, elbow, hip, knee, or ankle.

In some embodiments, the surgical procedure includes but is not limited to osteotomy, joint arthroplasty, total joint replacement, partial joint replacement, joint resurfacing, joint reconstruction, joint arthroscopy, joint replacement revision, meniscectomy, repair of a bone fracture, tissue grafting, and laminectomy. In some embodiments, the surgical procedure comprises repair of a ligament in a joint. In some embodiments, the surgical procedure comprises anterior cruciate ligament (ACL) or posterior cruciate ligament (PCL) repair. In some embodiments, the surgical procedure comprises a knee or a hip replacement.

In some embodiments, the methods, devices, and systems provided herein provides guidance or recommendation on various steps in the surgical procedure, including but not limited to where the cut a bone, where to place a joint replacement prothesis or graft, and determine the effectiveness of the placement of the prothesis or graft. In some embodiments, the guidance provided by the methods, devices, and systems provided herein improves the accuracy of the surgical procedure step. In some embodiments, the guidance provided by the methods, devices, and systems provided herein improves the accuracy of the surgical procedure step by at least 1%, 2%, 3%, 4%, 5%, 6%, 7%, 8%, 9%, 10%, 15%, 20%, 25%, 30%, 35%, 40%, 45%, or 50%. In some embodiments, the guidance provided by the methods, devices, and systems provided herein improves the accuracy of bone cutting by at least 1%, 2%, 3%, 4%, 5%, 6%, 7%, 8%, 9%, 10%, 15%, 20%, 25%, 30%, 35%, 40%, 45%, or 50%. In some embodiments, accuracy of the procedure is measured by deviation of at least one of location, rotation, or orientation of the body part before the surgical step and the after performing the guided or recommended step in the procedure.

In some embodiments, the methods provided herein are repeated throughout the surgical procedure to obtain information on location, rotation, and/or orientation of the object of interest during the surgical procedure. In some embodiments, the methods described herein provide a real-time or near real-time information on location, rotation, and/or orientation of the object of interest during the surgical procedure. In some embodiments, the methods described herein provide a real-time or near real-time tracking of the object of interest during the surgical procedure. In some embodiments, the methods provided herein are performed continuously during the surgical procedure.

In some embodiments, the methods, devices, and systems described herein may be used with multiple light beams. In some embodiments, the methods, devices, and systems described herein may be used with multiple crosshair-patterned light beams. In some embodiments, the use of multiple light beam patterns allows the methods, devices, and systems provided herein to expand the field of view and analyze a larger field of view. In some embodiments, minimally invasive surface markers may be used alternatively or in combination with the patterned light beam for the methods, devices, and systems described herein. In some embodiments, minimally invasive surface markers may be used similarly to the pattern from the light beam by the methods, devices, and systems described herein.

Processor

The methods, devices, and systems provided herein comprises a processor to control and integrate the function of the various components to register, track, and/or guide the object of interest. Provided herein are computer-implemented systems comprising: a digital processing device comprising: at least one processor, an operating system configured to perform executable instructions, a memory, and a computer program. The methods, devices, and systems disclosed herein are performed using a computing platform. A computing platform may be equipped with user input and output features. A computing platform typically comprises known components such as a processor, an operating system, system memory, memory storage devices, input-output controllers, input-output devices, and display devices. In some instances, a computing platform comprises a non-transitory computer-readable medium having instructions or computer code thereon for performing various computer-implemented operations.

Figure 14:
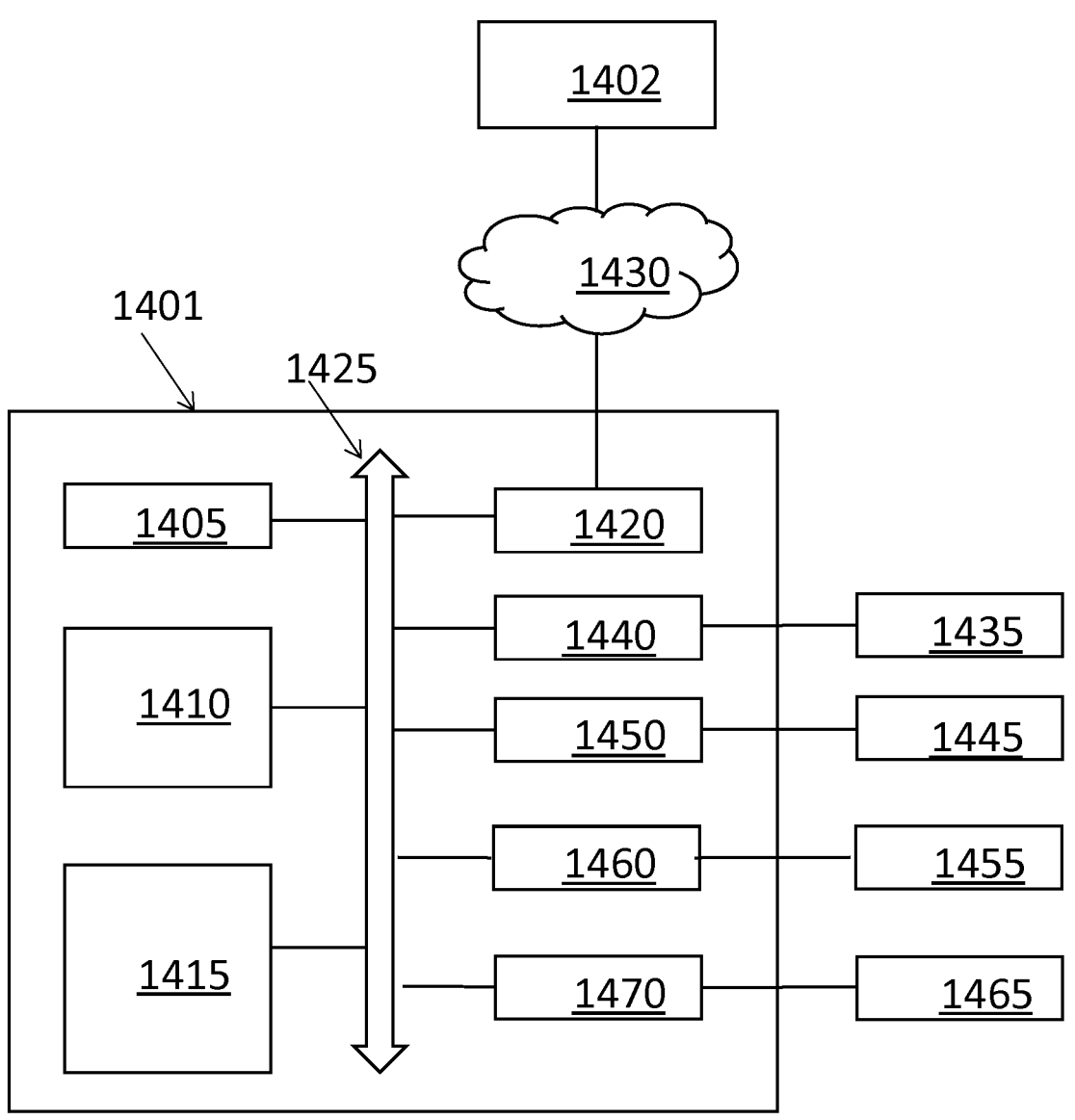
FIG. 14 shows an exemplary embodiment of a system as described herein comprising a device such as a digital processing device.

FIG. 14 shows an exemplary embodiment of a system as described herein comprising a device such as a digital processing device 1401. The digital processing device 1401 includes a software application configured to monitor the physical parameters of an individual. The digital processing device 1401 may include a processing unit 1405. In some embodiments, the processing unit may be a central processing unit ("CPU," also "processor" and "computer processor" herein) having a single-core or multi-core processor, or a plurality of processors for parallel processing or a graphics processing unit ("GPU"). In some embodiments, the GPU is embedded in a CPU die. The digital processing device 1401 also includes either memory or a memory location 1410 (e.g., random-access memory, read-only memory, flash memory), electronic storage unit 1415 (e.g., hard disk), communication interface 1420 (e.g., network adapter, network interface) for communicating with one or more other systems, and peripheral devices, such as a cache. The peripheral devices can include storage device(s) or storage medium(s) 1465 which communicate with the rest of the device via a storage interface 1470. The memory 1410, storage unit 1415, interface 1420 and peripheral devices are configured to communicate with the CPU 1405 through a communication bus 1425, such as a motherboard. The digital processing device 1401 can be operatively coupled to a computer network ("network") 1430 with the aid of the communication interface 1420. The network 1430 can comprise the Internet. The network 1430 can be a telecommunication and/or data network.

The digital processing device 1401 includes input device(s) 1445 to receive information from a user, the input device(s) in communication with other elements of the device via an input interface 1450. The digital processing device 1401 can include output device(s) 1455 that communicates to other elements of the device via an output interface 1460.

The CPU 1405 is configured to execute machine-readable instructions embodied in a software application or module. The instructions may be stored in a memory location, such as the memory 1410. The memory 1410 may include various components (e.g., machine readable media) including, by way of non-limiting examples, a random-access memory ("RAM") component (e.g., a static RAM "SRAM", a dynamic RAM "DRAM, etc.), or a read-only (ROM) component. The memory 1410 can also include a basic input/output system (BIOS), including basic routines that help to transfer information between elements within the digital processing device, such as during device start-up, may be stored in the memory 1410.

The storage unit 1415 can be configured to store files, such as image files and parameter data. The storage unit 1415 can also be used to store operating system, application programs, and the like. Optionally, storage unit 1415 may be removably interfaced with the digital processing device (e.g., via an external port connector (not shown)) and/or via a storage unit interface. Software may reside, completely or partially, within a computer-readable storage medium within or outside of the storage unit 1415. In another example, software may reside, completely or partially, within processor(s) 1405.

Information and data can be displayed to a user through a display 1435. The display is connected to the bus 1425 via an interface 1440, and transport of data between the display other elements of the device 1401 can be controlled via the interface 1440.

Methods as described herein can be implemented by way of machine (e.g., computer processor) executable code stored on an electronic storage location of the digital processing device 1401, such as, for example, on the memory 1410 or electronic storage unit 1415. The machine executable or machine-readable code can be provided in the form of a software application or software module. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

In some embodiments, a remote device 1402 is configured to communicate with the digital processing device 1401, and may comprise any mobile computing device, non-limiting examples of which include a tablet computer, laptop computer, smartphone, or smartwatch. For example, in some embodiments, the remote device 1402 is a smartphone of the user that is configured to receive information from the digital processing device 1401 of the device or system described herein in which the information can include a summary, sensor data, or other data. In some embodiments, the remote device 1402 is a server on the network configured to send and/or receive data from the device or system described herein.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

In the present description, any percentage range, ratio range, or integer range is to be understood to include the value of any integer within the recited range and, when appropriate, fractions thereof (such as one tenth and one hundredth of an integer), unless otherwise indicated. Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof. The use of the alternative (e.g., "or") should be understood to mean either one, both, or any combination thereof of the alternatives. As used herein, the terms "include" and "comprise" are used synonymously.

The term "about" or "approximately" can mean within an acceptable error range for the particular value as determined by one of ordinary skill in the art, which will depend in part on how the value is measured or determined, e.g., the limitations of the measurement system. For example, "about" can mean plus or minus 10%, per the practice in the art. Alternatively, "about" can mean a range of plus or minus 20%, plus or minus 10%, plus or minus 5%, or plus or minus 1% of a given value. Where particular values are described in the application and claims, unless otherwise stated, the term "about" means within an acceptable error range for the particular value that should be assumed. Also, where ranges and/or subranges of values are provided, the ranges and/or subranges can include the endpoints of the ranges and/or subranges.

The terms "determining", "measuring", "evaluating", "assessing," and "analyzing" are often used interchangeably herein to refer to forms of measurement and include determining if an element is present or not (for example, detection). These terms can include quantitative, qualitative or quantitative and qualitative determinations. Assessing is alternatively relative or absolute.

The terms "subject," "individual," or "patient" are often used interchangeably herein. A "subject" can be an animal. The subject can be a mammal. The mammal can be a human. The subject may have a disease or a condition that can be treated by a surgical procedure. In some cases, the subject is not necessarily diagnosed or suspected of being at high risk for the disease or a condition but undergoes a surgical procedure.

The term "in vivo" is used to describe an event that takes place in a subject's body.

The term "ex vivo" is used to describe an event that takes place outside of a subject's body. An "ex vivo" assay is not performed on a subject. Rather, it is performed upon a sample separate from a subject. An example of an "ex vivo" assay performed on a sample is an "in vitro" assay.

The section headings used herein are for organizational purposes only and are not to be construed as limiting the subject matter described.

EXAMPLES

The following examples are included for illustrative purposes only and are not intended to limit the scope of the invention.

Example 1: Tracking and Registering Using Markers

Provided herein is an exemplary embodiment of workflow for tracking and registering a knee joint using markers that are drilled into the in tibia and femur of the knee joint in the patient and protrude out from their placement site. The placement of the marker in order to track and register the bones of the knee joint is an invasive procedure that damages the tissue at and around the knee joint. The marker is used in marker-based tracking to track and register the knee joint and in robot-assisted surgical systems. Such invasive fixation of markers to bones may lead to complications, infections, nerve injury, and bone fracture. The marker fixation may reduce the flexibility during the procedure as the protruding markers may get in the way during the procedure. The surgical procedure may take longer to fix the marker into place than a markerless approach.

Example 2: Markerless Tracking and Registering

Provided herein is an exemplary embodiment of a method for markerless tracking and registering an object of interest. A light beam was projected onto a contour of an object of interest. Then, an image of the light beam projected onto the contour of the object was obtained using an imaging module. The obtained image was input into a software module for a processor. The image was segmented by applying convolution filters into segmented images. The segmented images were quantized, and 3D profiles were reconstructed from the quantized images. The reconstructed 3D profiles were converted to 2D profiles by transformation to a local coordinate system. Then, a feature vector was formed from the 2D profiles by concatenation and normalization. The object poses were predicted by applying machine learning to the feature vector. The methods and systems described herein requires shorter surgical time as the additional time to invasively place the large markers is not needed. The shorter surgical procedure time can result in better surgical outcomes, less tissue damage, and less complications for the patient.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A system for tracking an object in real-time or near real-time during a surgery, the system comprising:
   a memory; and
   a processor in communication with the memory and configured to:
   a) receive, during the surgery, a plurality of images of a patterned light beam passed through a patterned filter and projected onto the object during the surgery, wherein the plurality of images comprise a contour of the object;
   b) input the plurality of images into a software module during the surgery;
   c) determine, with the software module during the surgery, an output of a location, orientation, or rotation of the object in three-dimensional space; and
   d) generate, during the surgery, a three-dimensional visual representation of the object based at least in part on the location, orientation, or rotation of the object in three- dimensional space.

2. The system of claim 1, wherein the processor is configured to display the three-dimensional visual representation of the object.

3. The system of claim 1, wherein the processor is configured to repeat steps (a)-(c) to track the object during the surgery.

4. The system of claim 1, wherein the generating the three-dimensional visual representation provides real-time tracking of the object.

5. The system of claim 1, wherein the surgery comprises a robot-assisted surgery.

6. The system of claim 1, wherein the surgery comprises an orthopedic surgery.

7. The system of claim 1, wherein the surgery comprises an arthroplasty, a total joint replacement, or a partial joint replacement.

8. The system of claim 1, wherein the object comprises a knee joint, a hip joint, an elbow joint, a shoulder joint, an ankle joint, or a combination thereof.

9. The system of claim 1, wherein the system is configured for tracking the object without the use of a marker placed on the object.

10. The system of claim 1, wherein the patterned light beam comprises an infrared wave.

11. The system of claim 1, wherein the plurality of images are captured by a video camera.

12. The system of claim 1, wherein the three-dimensional visual representation of the object is registered to a prior image of the object obtained before the surgery.

13. The system of claim 12, wherein the prior image of the object comprises a computer tomography scan, a magnetic resonance imaging scan, an x-ray scan, a positron emission tomography scan, an ultrasound scan, or a combination thereof.

14. The system of claim 1, wherein a display comprising the three-dimensional visual representation of the object is configured to be manipulated by a user.

15. The system of claim 14, wherein the manipulation by the user comprises zooming in and out, rotating, or moving the display comprising the three-dimensional visual representation of the object.

16. The system of claim 1, wherein the software module comprises a neural network.

17. The system of claim 16, wherein the software module comprises a multilayer perceptron.

18. The system of claim 1, wherein the three-dimensional visual representation of the object comprises a recommendation, guidance, or instruction for performing the surgery.

19. A non-transitory computer-readable storage medium, having a computer executable instruction executable by one or more processors to:
   a) receive, during a surgery, a plurality of images of a patterned light beam passed through a patterned filter and projected onto an object during the surgery;

b) input the plurality of images into a software module, wherein the plurality of images comprise a contour of the object;

c) determine, with the software module, an output of a location, orientation, or rotation of the object in three-dimensional space during the surgery, based on the plurality of images; and d) generate a three-dimensional visual representation of the object based at least in part on the location, orientation, or rotation of the object in three-dimensional space during the surgery.

20. A system for real-time or near real-time tracking a joint during an orthopedic surgery, the system comprising:

a memory; and a processor in communication with the memory and configured to:

a) receive, during the orthopedic surgery, a plurality of images of a patterned light beam passed through a patterned filter and projected onto the joint during the orthopedic surgery;

b) input the plurality of images into a software module, wherein the plurality of images comprise a contour of the joint;

c) determine, with the software module, an output of a location, orientation, or rotation of the joint in three-dimensional space during the orthopedic surgery, based on the plurality of images;

d) generate a three-dimensional visual representation of the joint in real-time or near real-time based at least in part on the location, orientation, or rotation of the joint in three-dimensional space during the orthopedic surgery, wherein the three-dimensional visual representation of the joint is registered to an image of the joint; and e) display the three-dimensional visual representation of the joint, wherein the three-dimensional visual representation of the joint is configured to be manipulated by a user.

* * * * *